(12) United States Patent
Sun et al.

(10) Patent No.: US 11,959,912 B2
(45) Date of Patent: Apr. 16, 2024

(54) FLUORESCENCE IMMUNOCHROMATOGRAPHIC DETECTION CARD AND A PREPARATION METHOD THEREFOR AND USE THEREOF

(71) Applicant: Wuhan Newcando Biotechnology Co., Ltd., Wuhan (CN)

(72) Inventors: Honghao Sun, Wuhan (CN); Hui Zhu, Wuhan (CN); Changrong Zhou, Wuhan (CN)

(73) Assignee: Wuhan Newcando Biotechnology Co., Ltd., Wuhan (CN)

( * ) Notice: Subject to any disclaimer, the term of this patent is extended or adjusted under 35 U.S.C. 154(b) by 1426 days.

(21) Appl. No.: 16/336,042

(22) PCT Filed: May 26, 2017

(86) PCT No.: PCT/CN2017/086069
§ 371 (c)(1),
(2) Date: Mar. 22, 2019

(87) PCT Pub. No.: WO2018/120620
PCT Pub. Date: Jul. 5, 2018

(65) Prior Publication Data
US 2019/0219569 A1   Jul. 18, 2019

(30) Foreign Application Priority Data
Dec. 30, 2016 (CN) .......................... 201611258692.5

(51) Int. Cl.
*G01N 33/533* (2006.01)
*G01N 33/532* (2006.01)
(Continued)

(52) U.S. Cl.
CPC ......... *G01N 33/533* (2013.01); *G01N 33/532* (2013.01); *G01N 33/543* (2013.01);
(Continued)

(58) Field of Classification Search
CPC .. G01N 33/533; G01N 33/532; G01N 33/543; G01N 33/54388; G01N 33/587;
(Continued)

(56) References Cited

U.S. PATENT DOCUMENTS

| 2004/0087032 A1* | 5/2004 | Chandler | ............. | G01N 33/582 |
| | | | | 436/164 |
| 2009/0136918 A1* | 5/2009 | Newkirk | .............. | C12Q 1/6834 |
| | | | | 435/6.12 |

(Continued)

FOREIGN PATENT DOCUMENTS

| CN | 102841207 A | 12/2012 |
| CN | 103163297 A | 6/2013 |

(Continued)

OTHER PUBLICATIONS

CN 105652008 A English translation (Year: 2016).*

(Continued)

*Primary Examiner* — Christine T Mui
*Assistant Examiner* — Jonathan Bortoli
(74) *Attorney, Agent, or Firm* — Standley Law Group LLP; Adam J. Smith; Kenny W. Pung

(57) ABSTRACT

A fluorescence immunochromatographic detection card and a preparation method therefor and usage thereof is disclosed. The fluorescence immunochromatographic detection card comprises a treatment liquid A, a treatment liquid B, and a detection card. The treatment liquid A contains an antibody 15C4 that is coupled with a fluorescent microsphere. The treatment liquid B contains an antibody 13G12 that is coupled with biotin. The detection card comprises a detection line area and a quality control line area, and a streptavidin detection T line is fixed in the detection area, and an antibody quality control C line is immobilized in the quality control line area. The preparation method comprises: (1)

(Continued)

formulating the treatment liquid A; (2) formulating the treatment liquid B; and (3) drawing the line on the detection card. The fluorescence immunochromatographic detection card has characteristics such as high sensitivity, high specificity, and high stability, and can be applied to the rapid detection of disease markers.

5 Claims, 2 Drawing Sheets

(51) Int. Cl.
*G01N 33/543* (2006.01)
*G01N 33/58* (2006.01)
(52) U.S. Cl.
CPC ..... *G01N 33/54388* (2021.08); *G01N 33/587* (2013.01); *G01N 2333/58* (2013.01); *G01N 2800/325* (2013.01)
(58) Field of Classification Search
CPC ......... G01N 2333/58; G01N 2800/325; G01N 33/558
See application file for complete search history.

(56) References Cited

U.S. PATENT DOCUMENTS

| 2012/0122239 A1* | 5/2012 | Konrath | G01N 33/74 436/501 |
| 2016/0115229 A1* | 4/2016 | Azorsa | G01N 33/57492 530/389.7 |

FOREIGN PATENT DOCUMENTS

| CN | 103197074 A | * | 7/2013 | |
| CN | 103197074 A | | 7/2013 | |
| CN | 104714025 A | * | 6/2015 | .......... G01N 33/558 |
| CN | 105198996 A | | 12/2015 | |
| CN | 105652008 A | * | 6/2016 | |
| CN | 105652008 A | | 6/2016 | |
| CN | 106771168 A | | 5/2017 | |
| WO | 2008056034 A1 | | 5/2008 | |

OTHER PUBLICATIONS

CN 104714025 A English translation (Year: 2015).*
CN103197074A English translation (Year: 2013).*
Xiamen (CN 101392172) published Mar. 25, 2009, translated Dec. 5, 2023 (Year: 2009).*

* cited by examiner

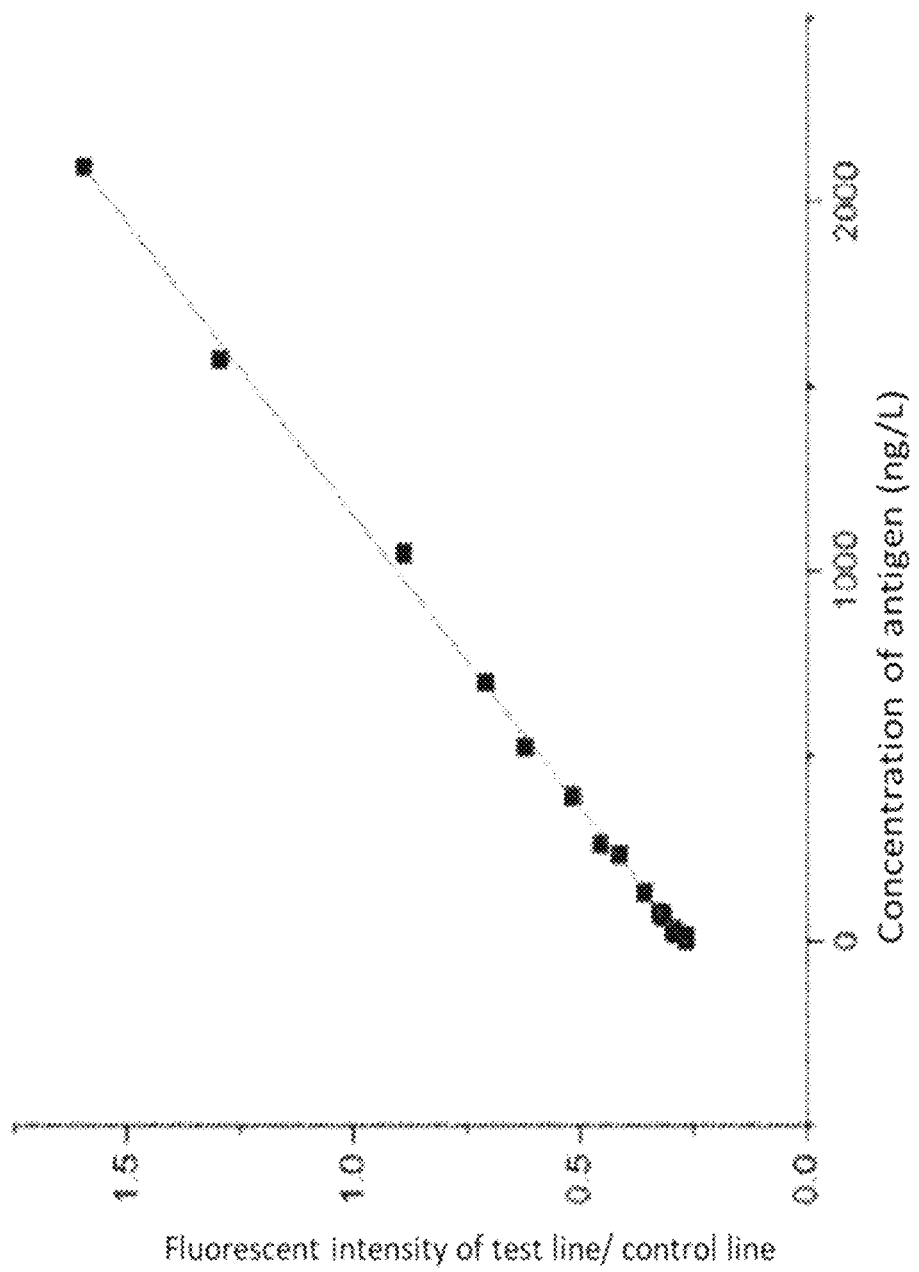

FLUORESCENCE IMMUNOCHROMATOGRAPHIC DETECTION CARD AND A PREPARATION METHOD THEREFOR AND USE THEREOF

CROSS-REFERENCE TO RELATED APPLICATIONS

This application claims priority to International Application No. PCT/CN2017/086069, filed on May 26, 2017, which claims the priority benefit of China Patent Application No. 201611258692.5, filed on Dec. 30, 2016. The contents of the above identified applications are incorporated herein by reference in their entirety.

FIELD OF THE TECHNOLOGY

The present invention belongs to the technical field of immunoassay, especially in relation to a fluorescence immunochromatographic detection card and its preparation and usage.

BACKGROUND

At present, there are some main methods for detecting disease biomarkers, including the Radioimmunoassay (RIA), Enzyme-Linked Immunosorbent Assay (ELISA), Electro-Chemiluminescence Immunoassay (ECLIA), Point-of-Care Testing (POCT), and so on.

RIA has higher errors for the instabilities of samples and the $^{125}$I marker, and as a result, the sensitivity and specificity of RIA are relatively low. Besides, RIA is not only complex and time-consuming but also it needs a lot of samples. Therefore, RIA isn't an ideal method for detecting disease markers. In recent years, ELISA has been widely used for diagnoses of clinical diseases; however, it has many limitations, such as many steps for an experiment, complex protocol operations, many influencing factors for results, difficulty of ensuring control, and lastly determining the optical density of sample color. In addition, ELISA is not as accurate and sensitive as the luminescence immune technology. So far, Roche Elesys electrochemical luminescence immunity analysis system is mainly adopted throughout the world for the detection of biomarkers in human serum because of its high sensitivity and quantitative accuracy. ECLIA has the disadvantage of complicated protocol operations, which is used for the determination of batch samples, and it is not suitable for medium and small scale hospitals and individuals. Furthermore, expensive machines and reagents needed for the test limit the extensive application of chemiluminescence immunoassay. The current detection card using POCT detects the disease biomarkers with simple operation, low cost, instant results, and a portable detecting instrument is, but the sensitivity is not satisfactory. Therefore, it is significant to develop a highly sensitive and universal detection card for the diagnosis of disease biomarkers.

For example, heart failure is the end stage of various cardiovascular diseases, which is in an extremely dangerous state with high death rates. If it is not diagnosed early and treated in time, the prognosis of the patients with heart failure will be poor. It is important that timely and accurate diagnosis is made for patients with heart failure, especially patients visiting to hospital emergency departments. Numerous studies have shown that NT-proBNP is a good marker for the diagnosis of heart failure. Determination for the concentration of NT-proBNP is significant in clinical diagnosis. NT-proBNP recommended by the European and American College of Cardiology is by far the best examination index to evaluate heart failure. Because the concentration of NT-proBNP in serum is extremely low, if the concentration of NT-proBNP is more than 300 ng/L by POCT, the result is considered positive. The detection cards that are made by conventional methods for detecting the NT-proBNP have low sensitivity, because a low concentration of NT-proBNP is hard for T-Xay to detect. Therefore, it is significant to develop a highly sensitive detection card for detection for NT-proBNP by POCT.

SUMMARY

The present application aims to overcome the problems of the prior art and provide a highly sensitive, specific and stable fluorescence immunochromatographic detection card and preparation method therefor and usage thereof in the rapid detection of disease biomarkers.

In order to solve the technical problems described as above, the invention offers technical proposals as follows:

A fluorescence immunochromatographic detection card, comprising a treatment liquid A, a treatment liquid B, and a detection card, the treatment liquid A contains one kind of antibody 1 that is coupled with a fluorescent microsphere and targets an antigen to be tested; the treatment liquid B contains one kind of antibody 2 that is coupled with biotin and targets the same antigen to be tested, the detection card comprises a detection line area and a quality control line area, and a streptavidin detection T line is fixed in the detection area, and an antibody quality control C line is immobilized in the quality control line area.

In the preferred embodiment, the fluorescent microsphere is the fluorescent microsphere embedding fluorescent molecules, the T line is fixed with streptavidin, and the C line is immobilized with goat anti-mouse IgG.

In the preferred embodiment, the antigen to be tested is NT-proBNP.

In the preferred embodiment, the antibody 1 is antibody 14C4 or antibody 5B6, antibody 2 is antibody 13G12 or antibody 15F11.

As a single inventive concept, the present invention provides a preparation method of the fluorescence immunochromatographic detection card, including the following steps.

(1) Preparing the Treatment Liquid A.

(1.1) To carboxylated fluorescent microspheres, EDC and NHS were added to activate it, after the activation, and then the mixture solution was centrifuged. After the precipitate was collected, the precipitate was dispersed in PB to acquire the dispersion liquid of activated carboxylated fluorescent microspheres.

(1.2) To the activated the dispersion liquid of activated carboxylated fluorescent microspheres prepared in step (1.1), antibody 1 was added for a coupling reaction. After centrifugation, the sediment was collected, which was antibodies 1 coupled with carboxylated fluorescent microspheres.

(1.3) To antibodies 1 coupled with the carboxylated fluorescent microspheres prepared in step (1.2), BSA was added to block the surface of the activated fluorescent microspheres. After blocking reaction, the mixture solution was then centrifuged to get the sediment, the sediment was added antibody storage buffer to acquire the treatment liquid A.

(2) Preparing the Treatment Liquid B.

Antibody 2 was added into biotin solution for a coupling reaction, and then the mixture solution was diluted, and then dialyzed to eliminate excess unreacted biotin. The resultant was collected to acquire the treatment of liquid B.

(3) Drawing the Line on the Detection Card.

The T line was drawn on the test area of detection card with streptavidin solution, The C line was drawn on the quality control area of detection card with antibody solution.

In the preferred embodiment, in the step (1.1), the mass ratio between EDC and carboxylated fluorescent microspheres is 1:1, the mass ratio between NHS and carboxylated fluorescent microspheres is 1:1, and the activation time is 45 minutes.

In the preferred embodiment, in the step (1.2), the mass ratio between antibody 1 and carboxylated fluorescent microspheres is 3:500, and the coupling reaction is at 4° C. for 8 hours-12 hours.

In the step (2), a molecular ratio between the antibody 2 and the biotin is 1:50-200, the coupling reaction time is 4 hours, and the dialysis is at 4° C. for 48 hours.

In the preferred embodiment, in the step (3), the concentration of the streptavidin solution is 10 μg/pL, the concentration of the antibody solution is 1 μg/pL.

As a single inventive concept, the present invention provides the usage of the fluorescence immunochromatographic detection card in the early diagnosis of diseases.

As a single inventive concept, the present invention provides the usage of the fluorescence immunochromatographic detection card that is made by the preparation method in the early diagnosis of diseases.

Compared with the prior art, the present invention has beneficial effects as follows.

1. The invention provides a highly sensitive detection card of antigen being tested and its preparation method based on fluorescence immunochromatography and biotin-streptavidin marking technology. Both streptavidin and biotin can bind to protein (antigen, antibody, and enzyme) and fluorescein without influence on the activity of the latter, which is an ideal marker. An antibody is capable of conjugating with more than 10 biotin molecules or streptavidin, and biotin molecules or streptavidin have the ability to bind enzymes or fluorescein. We take advantage of the strong affinity between biotin and streptavidin, as well as, several ligand-binding sites of streptavidin to make a biological amplification system, which amplifies multistage signal. The Biotin-Avidin-System (BAS) system characterized by high sensitivity, specificity and stability improves the specificity and sensitivity of immunoassay for quick detecting the trace amount of substance. It overcomes the difficulty in a trace analysis because of low concentration.

2. The goal of the present invention is achieved by the technical proposal as follow. The fluorescent microspheres which were made by embedding methods have stable performance, high fluorescence intensity, and sensitivity. Fluorescent microspheres coupled with streptavidin are effective, homogeneous, stable, and general. The biotinylated antibodies couple with antigens in the samples, and then drawing the line with streptavidin solution. Antibody 1 and antibody 2 are promoted to capture the antigen of samples via the strong streptavidin-biotin interaction, and then form an immune complex as a sandwich structure. By combination between biotinylated immune complex and streptavidin fixed in the T line, the fluorescence intensity of the T line and the C line are determined separately. The fluorescence intensity of the T line to the fluorescence intensity of the C line ratio is used to quantitate the concentration of disease biomarkers. Streptavidin-biotin is the strongest and the most specify combination, which ensures coating effect and specific test results.

3. The machine required by the detection card of the present invention is small in volume, easy to carry, simple to operate and easy to master. It doesn't even need the a professional to operate, and the cost of the test is low. Besides, according to different detection samples, different disease markers can be detected by changing the treatment of liquid A or the treatment of liquid B.

4. The invention is specially applied to the rapid detection of NT-proBNP. Detection card made by combining a biotin-streptavidin linkage and immunofluorescence can sensitively detect the minute amount of NT-proBNP in samples, which is an accurate and quick approach to diagnose patients with heart failure. By using streptavidin immobilized in the detection card, the detection card sensitively and specifically quantitates the NT-proBNP. The minimum detectable concentration reaches 20 ng/ml. Besides, after the freeze-drying process, fluorescent microspheres labeled by antibody 15C4 and antibody 13G12 labeled by biotin have good stability in the present invention. The detection card which is kept in normal temperature preservation has the same good results as the one which is kept in 4° C. preservation.

BRIEF DESCRIPTION OF THE DRAWINGS

FIG. 2 is a calibration curve of the fluorescence immunoassay at different NT-proBNP concentrations by using the fluorescence immunochromatographic detection card in the embodiment 1.

DETAILED DESCRIPTION

Figure 1:
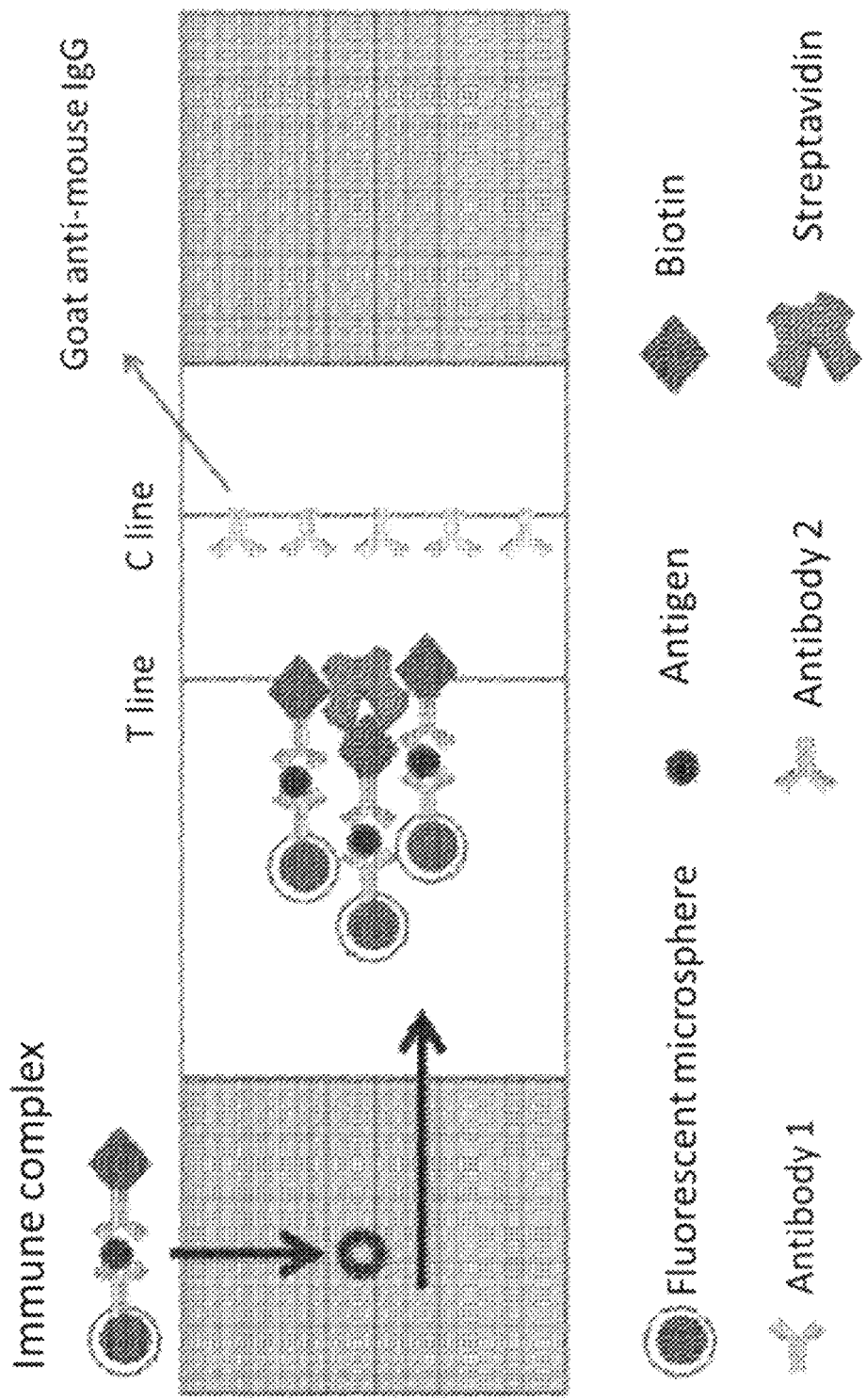
FIG. 1 shows a schematic illustration of the principle of the fluorescence immunochromatographic detection card.

The present invention is further described in detail below through embodiments accompanied with drawings, and it will be apparent that the described embodiments are merely part of the embodiments of the present invention and are not intended to be exhaustive. The present invention is not limited by the materials, reaction conditions or parameters. All other embodiments obtained by those of ordinary skill in the art based on technical principles with alternative materials or reaction conditions are within the scope of the present invention. Accordingly, those skilled in the art could use other materials or reaction conditions to prepare detection cards for disease markers by combining a biotin-streptavidin linkage and immunofluorescence within the spirit and scope of the invention.

Embodiment 1

The fluorescence immunochromatographic detection card comprises a treatment liquid A, a treatment liquid B, and a detection card, the treatment liquid A contains an antibody 15C4 that is coupled with a fluorescent microsphere; the treatment liquid B contains an antibody 13G12 that is coupled with a biotin, the detection card comprises a detection line area and a quality control line area, and a streptavidin detection T line is fixed in the detection area, and an antibody quality control C line is immobilized in the quality control line area.

The preparation method of the fluorescence immunochromatographic detection card described as above includes the following steps.

(1) Preparing the Treatment Liquid A.

(1.1) 200 μL of 10 mg/ml carboxylated fluorescent microspheres centrifuged at 14400 rpm for 10 minutes was washed with 1000 μL MES (pH 6.0), and was centrifuged at 14400 rpm for 8 minutes, removed the MES, and repeated the wash step once more. 0.0110 g EDC was dissolved into 110 μL of MES. 0.0034 g NHS was dissolved into 34 μL of MES. The carboxylated fluorescent microspheres were added to 125 μL of MES, 25 μL of EDC prepared as described above and 25 μL of NHS prepared as described above. The mixture solution was stirred at 60 rpm at room temperature and activated for 45 minutes, and then the mixture solution was washed with 10 mM PB (pH7.4), and centrifuged at 14400 rpm for 10 minutes, and repeat the wash step once more. Finally, the product was dispersed in 1250 μL PB to acquire the dispersion solution of activated carboxylated fluorescent microspheres. The term "MES" as used in the present description refers to 2-morph-olinoeth-anesulfonic acid. The term "EDC" as used in the present description refers to 1-ethyl-3-(3-dimethylamino-propyl) carbodiimide hydrochloride. The term "NHS" as used in the present description refers to N-hydroxy-succinimide. The term "PB" as used in the present description refers to Phosphate Buffer.

(1.2) To the activated carboxylated fluorescent microspheres prepared in step (1.1), 1.64 μL of antibody 15C4 (9.2 mg/ml) was added for a coupling reaction at 4° C. overnight. The mixture solution was then centrifuged at 14400 rpm for 8 minutes to get sediment. The sediment was antibodies 15C4 coupled with carboxylated fluorescent microspheres.

(1.3) To antibody 15C4 coupled with carboxylated fluorescent microspheres prepared in step (1.2), were added to 250 μL of BSA to block the surface of the fluorescent microspheres, and the resultant was to be conjugated for 2 hours at room temperature. The mixture solution was then centrifuged at 14400 rpm for 8 minutes. After the sediment was collected, the sediment was washed by 1000 μL of PB (10 mM) and added 250 μL of antibody storage buffer to store at 4° C. The term "BSA" as used in the present description refers to Bull Serum Albumin.

(2) Preparing the Treatment Liquid B.

To 100 μg of antibody 13G12, biotin was added to for the coupling reaction. The molecular ratio between antibody 13G12 and biotin is 1:100 in 50 μL volume for 4 hours at room temperature. The resultant was diluted to 250 μL, and dialyzed at 4° C. for 48 hours to eliminate the excess unreacted biotin; the resultant is the treatment liquid B.

(3) Drawing the Line on the Detection Card.

Streptavidin solution (10 μg/pL) was immobilized onto the test area as the T line. A goat anti-mouse IgG secondary antibody was immobilized to the quality control area as the C line.

The fluorescence immunochromatographic detection card is used to determine the NT-proBNP, including the following steps.

S1. The treatment liquid A prepared in step (1) mixed with a human blood sample, antibody 15C4, and NT-proBNP formed antigen-antibody complex, then was added to the treatment liquid B prepared in step (1), and then antibody 13G12 bound to NT-proBNP to form a sandwich structure. The mixture sample was dripped into the sample well. FIG. 1 shows a schematic illustration of the principle of determination.

S2. Determination of results: the fluorescence curve was obtained by using fluorescence immunoassay quantitative analyzer, and then got the ratio between T and C by using a particular algorithm. The concentration of the NT-proBNP could be calculated by a standard concentration curve. The results are shown as the Table 1 and FIG. 2.

TABLE 1 the ratios of T line to C line fluorescence intensity according to different concentration of NT-proBNP

| Number | T/C | The concentration of antigen |
| --- | --- | --- |
| 1 | 1.5960 | 2097 |
| 2 | 1.2951 | 1573 |
| 3 | 0.8872 | 1049 |
| 4 | 0.7091 | 699 |
| 5 | 0.6206 | 525 |
| 6 | 0.5162 | 393 |
| 7 | 0.4538 | 262 |
| 8 | 0.4134 | 233 |
| 9 | 0.3571 | 131 |
| 10 | 0.3231 | 78 |
| 11 | 0.3153 | 66 |
| 12 | 0.2956 | 33 |
| 13 | 0.2917 | 26 |
| 14 | 0.2882 | 20 |
| 15 | 0.2651 | 16 |
| 16 | 0.2412 | 0 |

Table 1 and FIG. 2 show that the present invention applied a fluorescent protein modified by streptavidin as a tracer to conjugate the biotin-labeled anti-NT-proBNP to facilitate the detection of NT-proBNP in human serum for rapid and accurate diagnosis of heart failure. The detection card using streptavidin immobilized in the test area has a reasonable structure to quantitate the concentration of the NT-proBNP.

Finally, it should be understood that the above embodiments are only used to explain, but not to limit the technical solution of the present invention. In spite of the detailed description of the present invention with referring to above preferred embodiments, it should be understood that various modifications, changes or equivalent replacements can be made by those skilled in the art without departing from the scope of the present invention and covered in the claims of the present invention.

What is claimed is:

1. A preparation method of a fluorescence immunochromatographic detection card comprising a treatment liquid (A), a treatment liquid (B), and a detection card, in which the treatment liquid (A) contains a first antibody that is coupled with a carboxylated fluorescent microsphere formed by embedding fluorescent molecules and the first antibody targets an antigen to be tested; the treatment liquid (B) contains a second antibody that is coupled with biotin and the second antibody targets the antigen to be tested; the first antibody is an antibody 15C4, and the second antibody is an antibody 13G12; the detection card comprises a detection line area and a quality control line area, a streptavidin detection T line is fixed in the detection area, and an antibody quality control C line is immobilized in the quality control line area;

wherein the preparation method comprises the following steps:

(1) preparing the treatment liquid (A);

(1.1) adding a first quantity of 1-ethyl-3-(3-dimethyl-amino-propyl) carbodiimide hydrochloride and a second quantity of N-hydroxy-succinimide into a third quantity of carboxylated fluorescent microspheres thereby obtaining a first mixture solution and performing activation thereby obtaining a fourth quantity of activated carboxylated fluorescent microspheres, after the activation, centrifuging the first mixture solution, and then collecting a precipitate of the first mixture solution in a phosphate buffer, and dispersing the precipitate of the first mixture solution in the phosphate buffer to acquire a dispersion liquid of the activated carboxylated fluorescent microspheres;

(1.2) adding a fifth quantity of the first antibody into the dispersion liquid of the activated carboxylated fluorescent microspheres prepared in the step (1.1) thereby obtaining a second mixture solution for a coupling reaction, and then centrifuging the second mixture solution, and collecting a sediment of the second mixture to acquire a sixth quantity of the first antibodies coupled with the activated carboxylated fluorescent microspheres;

(1.3) adding a seventh quantity of bull serum albumin to the sixth quantity of the first antibodies coupled with the activated carboxylated fluorescent microspheres prepared in (1.2) to block a surface of the activated carboxylated fluorescent microspheres thereby obtaining a third mixture solution, and then centrifuging the third mixture solution and collecting a sediment of the third mixture solution, adding an antibody storage buffer into the third mixture solution to acquire the treatment liquid (A);

(2) preparing the treatment liquid (B):

adding an eighth quantity of the second antibody into a biotin solution thereby obtaining a fourth mixture solution for the coupling reaction, and then diluting the fourth mixture solution and dialyzing the fourth mixture solution to eliminate excess unreacted biotin, collecting samples of the fourth mixture solution to acquire the treatment liquid (B);

(3) drawing the line on the detection card;

immobilizing a streptavidin solution onto the test area to form the T line, and immobilizing an antibody solution onto the quality control line to form the C line.

2. The preparation method of the fluorescence immunochromatographic detection card according to claim 1, wherein in the step (1.1), a mass ratio between the first quantity of 1-ethyl-3-(3-dimethylamino-propyl) carbodiimide hydrochloride and the carboxylated fluorescent microspheres is 1:1, a mass ratio between the second quantity of N-hydroxy-succinimide and the carboxylated fluorescent microspheres is 1:1, and an activation time is 45 minutes.

3. The preparation method of the fluorescence immunochromatographic detection card according to claim 1, wherein in the step (3), a concentration of the streptavidin solution is 10 µg/pL, a concentration of the antibody solution is 1 µg/pL.

4. The preparation method of the fluorescence immunochromatographic detection card according to claim 1, wherein the T line is fixed with streptavidin, and the C line is immobilized with goat anti-mouse IgG.

5. The preparation method of the fluorescence immunochromatographic detection card according to claim 1, wherein the antigen is N-terminal prohormone of brain natriuretic peptide.

\* \* \* \* \*